US011951085B2

(12) United States Patent
Jacobson

(10) Patent No.: US 11,951,085 B2
(45) Date of Patent: Apr. 9, 2024

(54) METHODS OF TREATING INJURIES OR CONDITIONS RELATED TO CNS EDEMA

(71) Applicant: BIOGEN CHESAPEAKE LLC, Cambridge, MA (US)

(72) Inventor: Sven Martin Jacobson, New York, NY (US)

(73) Assignee: REMEDY PHARMACEUTICALS, INC., New York, NY (US)

( * ) Notice: Subject to any disclaimer, the term of this patent is extended or adjusted under 35 U.S.C. 154(b) by 225 days.

(21) Appl. No.: 17/488,591

(22) Filed: Sep. 29, 2021

(65) Prior Publication Data

US 2022/0125750 A1 Apr. 28, 2022

Related U.S. Application Data

(62) Division of application No. 15/763,932, filed as application No. PCT/US2016/055988 on Oct. 7, 2016, now abandoned.

(60) Provisional application No. 62/238,461, filed on Oct. 7, 2015.

(51) Int. Cl.
| | | |
|---|---|---|
| *A61K 31/64* | (2006.01) | |
| *A61K 9/00* | (2006.01) | |
| *A61K 31/166* | (2006.01) | |
| *A61K 31/18* | (2006.01) | |
| *A61K 31/451* | (2006.01) | |
| *A61K 47/26* | (2006.01) | |
| *A61P 9/10* | (2006.01) | |

(52) U.S. Cl.
CPC ............ *A61K 31/18* (2013.01); *A61K 9/0019* (2013.01); *A61K 31/166* (2013.01); *A61K 31/451* (2013.01); *A61K 31/64* (2013.01); *A61K 47/26* (2013.01)

(58) Field of Classification Search
CPC ...... A61K 31/166; A61K 31/18; A61K 31/64; A61P 9/10
See application file for complete search history.

(56) References Cited

U.S. PATENT DOCUMENTS

| | | | |
|---|---|---|---|
| 5,856,360 A | 1/1999 | Salzman et al. | |
| 8,277,845 B2 | 10/2012 | Jacobson | |
| 8,557,867 B2 | 10/2013 | Simard | |
| 8,946,293 B2* | 2/2015 | Jacobson | A61K 9/0019 514/593 |
| 2005/0246000 A1* | 11/2005 | Larnard | A61F 7/10 607/104 |
| 2006/0276411 A1 | 12/2006 | Simard et al. | |
| 2013/0203853 A1* | 8/2013 | Jacobson | A61P 9/06 514/593 |

FOREIGN PATENT DOCUMENTS

| | | |
|---|---|---|
| JP | 2005-534285 | 11/2005 |
| JP | 2013-532658 A | 8/2013 |
| WO | 2003079987 A2 | 10/2003 |
| WO | 2012012347 A2 | 1/2012 |

OTHER PUBLICATIONS

Nehring SM, Tadi P, Tenny S. Cerebral Edema. [Updated Jul. 31, 2022]. In: StatPearls [Internet]. Treasure Island (FL): StatPearls Publishing; Jan. 2023. Available from: https://www.ncbi.nlm.nih.gov/books/NBK537272/. (Year: 2022).*
Zazulia et al. ("Progression of Mass Effect After Intracerebral Hemorrhage." Stroke, (1999);30:1167-1173. https://doi.org/10.1161/01.STR.30.6.1167.) (Year: 1999).*
Ospel et al. "Strength of Association between Infarct Volume and Clinical Outcome Depends on the Magnitude of Infarct Size: Results from the ESCAPE-NA1 Trial." AJNR Am J Neuroradiol. Aug. 2021;42(8):1375-1379. doi: 10.3174/ajnr.A7183. Epub Jun. 24, 2021. PMID: 34167959; PMCID: PMC8367613. (Year: 2021).*
Walberer et al., "Midline-shift Corresponds to the Amount of Brain Edema Early After Hemispheric Stroke—An MR Study in Rats", J. Neurosurg Anesthesiol, 2007, vol. 19, No. 2, pp. 105-110.
Brain Nursing, 2013, vol. 29, No. 1, pp. 29-31.
Japanese Notice of Reasons for Rejection issued in 2021-022562 dated Jan. 18, 2022, 10 pages.
Eurasian Office Action issued in applcation No. 201890893 dated Jul. 6, 2022 , 7 pages.
Bolus, 2022, 2 pages. https://en.wikipedia.org/wiki/Bolus.
Wikipedia, Glibenclamide, 2022, 5 pages. https://en.wikipedia.org/wiki/Glibenclamide.
Wikipedia, Central nervous system, 2022, 11 pages.https://en.wikipedia.org/w/index.php?title=Central_nervous_system&oldid=6239202 57.
O.V. Vasilevskaya, Combined stroke, Practical Medicine, Jun. 3, 2007(22), p. 5-7.
Korshunov Nikolai Borisovich and Garmashov Yuriy Anatolievich, "Decompressive craniotomy in severe brain injury in children" Modern medicine: topical issues, 2014, 7 pages.
Kruglov, "Displacement of median structures | Lateral dislocation", accessed 2022, 3 pages (https://radiographia.info/article/smeshchenie-sredinnykh-struktur-lateralnaya-dislokatsiya).
"Ischemic Stroke," https://www.krasotaimedicina.ru/diseases/zabolevanija_neurology/ischemic-stroke, 2022.
Pallan T.V. et al. "Glyburide in Treating Malignant Cerebral Edema. Blocking Sulfonyl Urea One (SUR1) Receptors", Journal of Vascular and Interventional Neurology, 2014, vol. 7, issue 4, pp. 22-24.

(Continued)

*Primary Examiner* — Jeffrey S Lundgren
*Assistant Examiner* — Chris E Simmons
(74) *Attorney, Agent, or Firm* — ROTHWELL, FIGG, ERNST & MANBECK, P.C.

(57) ABSTRACT

The present technology is related to reducing or treating neurological swelling and related conditions with SUR1-TRPM4 channel inhibitors. In some embodiments, the methods include: reducing late neurological deterioration or preventing death, reducing cerebral midline shift, reducing the degree of disability in a subject, counteracting blood glucose levels in a subject receiving a SUR1-TRPM4 channel inhibitor, preventing brain swelling, monitoring liver enzyme activity along with treating injury or conditions related to CNS edema, or monitoring cardiac activity along with treating injury or conditions related to CNS edema.

20 Claims, 4 Drawing Sheets

(56) References Cited

OTHER PUBLICATIONS

Kimberly W.T. et al. "Glyburide is Associated with Attenuated Vasogenic Edema in Stroke Patients", Neurocrit Care, 2013, vol. 20, issue 2, pp. 193-201.
International Search Report cited in PCT/US2016/055988, dated Mar. 2, 2017, 4 pages.
English translation of Chinese First Office Action cited in application No. 201680066630.6 dated Jan. 6, 2020, 6 pages.
Sheth et al: "Exploratory analysis of glyburide as a novel therapy for preventing brain swelling.", Neurocrit Care, (2014), vol. 21, pp. 43-51.
Kurland et al: "Glibenclamide for the treatment of acute CNS injury.", Pharmaceuticals, vol. 6, (2013), pp. 1287-1303.
Partial European Search Report cited in 16854422.9 dated Apr. 24, 2019, 9 pages.
Official Action cited in EA application 201890893 dated Jul. 5, 2019, 3 pages, translation only.
Simard et al., "Newly expressed SUR1-regulated NCca-ATP channel mediates cerebral edema after ischemic stroke", Nat. Med. Apr. 2006; 12 (4); 433-440.
Notice of Reasons for Rejection issued in Japanese Application No. 2018-517841 dated Sep. 29, 2020, 5 pages.
The Iowa Clinic, "Traumatic Brain Injury (TBI)." https://www.iowaclinic.com/webres/File/traumatic-brain-injury.pdf, 2013.
Wintermark (J Am Coll Radiol 2015; 12:31-e14), 2015.
Simard et al., "Glibenclamide-10-h Treatment Window in a Clinically Relevant Model of Stroke", Trans.Stroke.Res., 2012, vol. 3, p. 286-295.

* cited by examiner

METHODS OF TREATING INJURIES OR CONDITIONS RELATED TO CNS EDEMA

CROSS REFERENCE TO RELATED APPLICATIONS

This application is a divisional of U.S. Ser. No. 15/763,932 filed Mar. 28, 2018 (371(c) date of Nov. 8, 2018), which claims the benefit of 35 U.S.C. 371 National Phase Entry Application from PCT/US2016/055988, filed Oct. 7, 2016, which claims the benefit of U.S. Provisional Patent Application No. 62/238,461 filed on Oct. 7, 2015, the disclosures of which are incorporated herein in their entireties by reference.

BACKGROUND

Following a spinal cord injury, cardiac arrest, liver failure, intraventricular hemorrhage, neurosurgery, traumatic brain injury, stroke (ischemic and/or hemorrhagic), infection, cerebral malaria, or other similar injury or ailment or any form of cerebral ischemia, subjects can suffer from space-occupying brain edema (swelling), or in the case of spinal cord injury, spinal cord edema. Life threatening cerebral swelling occurs in up to 8% of all hospitalized ischemic stroke patients and up to 15% of all middle cerebral artery stroke patients. In subjects that suffer from a stroke, cerebral swelling presents itself, usually, a few days after the stroke and generally peaks on the $2^{nd}$ or $3^{rd}$ day.

Cerebral swelling increases intracranial pressure and can prevent blood from flowing to the brain, thereby depriving the brain of oxygen. Brain swelling can also block the exit routes of the brain and prevent fluids from leaving the brain. Moreover, as intracranial pressure builds within the skull, formerly healthy brain tissue is destroyed and transtentorial or uncal herniation can occur. Swelling within and around the brain can also cause morbidity and brain death, as well as secondary neurological disorders and the death of the subject.

Cerebral swelling can be associated with two separate molecular and physiological processes, namely cellular swelling of the neurons and astrocytes, and the transcapillary influx of ions and fluids to the site of the injury. Cellular swelling of the neurons and astrocytes occurs as a result of ion gradient changes between the cells and the extracellular space. One ion channel that is associated with cellular swelling is the $NC_{CA-ATP}$ channel, also known as the SUR1-TRPM4 channel. This channel is a non-selective $Ca^{2+}$ activated ATP sensitive cation channel that is activated when neuronal cells are depleted of intracellular ATP. The $NC_{CA-ATP}$ channel is believed to be composed of regulatory subunits, including a sulfonylurea type receptor 1 (SUR1) and a pore subunit related to transient receptor potential cation channel subfamily M member 4 (TRPM4).

Minimizing the extent of brain swelling is a major concern of physicians when treating subjects that suffer from conditions or diseases where brain edema can occur. However, treating brain edema is particularly difficult because of the prolonged time periods associated with swelling, the brain's overall functioning, and the placement of the brain within the skull. Therefore, providing treatments that reduce the extent of brain edema would be advancement in the art.

SUMMARY

With this background in mind, the present disclosure is drawn to methods of reducing or treating CNS edema such as brain swelling, spinal cord swelling, and/or associated conditions.

In one embodiment, a method of reducing the incidence of late neurological deterioration (or death) in a subject following an injury or condition related to CNS edema is presented. The method includes administering one or more continuous infusion of a SUR1-TRPM4 channel inhibitor to the subject following the subject experiencing the injury or condition related to CNS edema and lasting for at least 72 hours after starting the continuous infusion thereby reducing late neurological deterioration.

In another embodiment, a method of reducing cerebral midline shift in a subject following an injury or condition related to cerebral edema is presented. The method includes administering to a subject a SUR1-TRPM4 channel inhibitor following the subject experiencing the injury or condition related to cerebral edema, and performing a decompressive craniectomy on the subject.

In yet another embodiment, a method of improving a degree of disability in a subject that has suffered from an injury or condition related to CNS edema is presented. The method includes administering one or more continuous infusion of a SUR1-TRPM4 channel inhibitor to a subject following the subject suffering from an injury or condition related to CNS edema. Additional steps include establishing an initial degree of disability for the subject based on a first scoring system or test, and determining a second degree of disability after a period of time from when initial degree of disability was determined using a second scoring system or test. In one example, the first and second scoring system or test can be the same, or alternatively, can be different. In one specific example, a scoring system is used for the first scoring system (or test).

In another embodiment, a method of counteracting a decline in blood glucose levels in a subject that is receiving a SUR1-TRPM4 channel inhibitor can include administering one or more continuous infusion of the SUR1-TRPM4 channel inhibitor to the subject, and co-administering a dextrose solution to the subject.

In another example, a method of preventing or reducing CNS edema in a subject at a high risk of severe brain or spinal cord swelling following an injury or condition related to CNS edema can include determining whether the subject is at a high risk for severe brain or spinal cord swelling, and administering a SUR1-TRPM4 channel inhibitor to the subject once the subject is determined to be at high risk for severe brain swelling.

In another example, a method of safely delivering glyburide to a subject can include administering one or more continuous infusion of glyburide to the subject, and measuring liver enzyme levels while continuing administration of the glyburide.

In another example, a method of monitoring cardiac activity when a sulfonylurea agent is administered to a subject can include administering one or more continuous infusion of the sulfonylurea to the subject, and performing an electrocardiogram on the subject to monitor the subject's heart.

In another example, a method delivering glyburide to a subject can include intravenously administering glyburide to the subject, and monitoring blood glucose, liver enzymes, and QTc during while intravenously administering the glyburide to the subject.

In another example, a method of treating a subject suffering from a large hemispheric infarction can include administering to the subject a therapeutically effective amount of an intravenous SUR1-TRPM4 channel inhibitor. The subject can be less than 71 years of age and the treating can result in improved functional outcomes as measured by one or more outcomes scales.

In another example, a method of treating a subject suffering from a large hemispheric infarction can include administering to the subject a therapeutically effective amount of an intravenous SUR1-TRPM4 channel inhibitor. The subject can have a lesion volume of at least about 100 cc, or an ASPECTS score of less than or equal to 5, or both.

In another example, a method of treating a subject suffering from a large hemispheric infarction can include administering to the subject a therapeutically effective amount of an intravenous SUR1-TRPM4 channel inhibitor. The administering can be initiated in 9 hours or less from the time of the index stroke or when the subject was last observed as normal.

In another example, a method of treating a subject suffering from a traumatic brain injury can include administering to said subject a therapeutically effective amount of an intravenous SUR1-TRPM4 channel inhibitor. The subject, prior to treatment, can show radiological evidence of intracerebral blood induced by said traumatic brain injury.

In another example, a method of testing a treat to treat LHI can include enrolling subjects at least 18 years old with radiologically defined LHI; treating the subjects with a SUR1-TRPM4 channel inhibitor or matching placebo for up to about 72 hours, beginning 9 hours or less from the stroke or the last time observed normal; and assessing the mRS. The method can be considered successful if a statistically significant result favoring drug is detected in subjects 70-years old or younger, or a descriptive benefit is detected in subjects greater than 70-years old.

BRIEF DESCRIPTION OF THE DRAWINGS

Reference will now be made to the exemplary embodiments illustrated, and specific language will be used herein to describe the same. It will nevertheless be understood that these drawings merely depict exemplary embodiments and are not, therefore, to be considered limiting of its scope.

DETAILED DESCRIPTION

Figure 1:
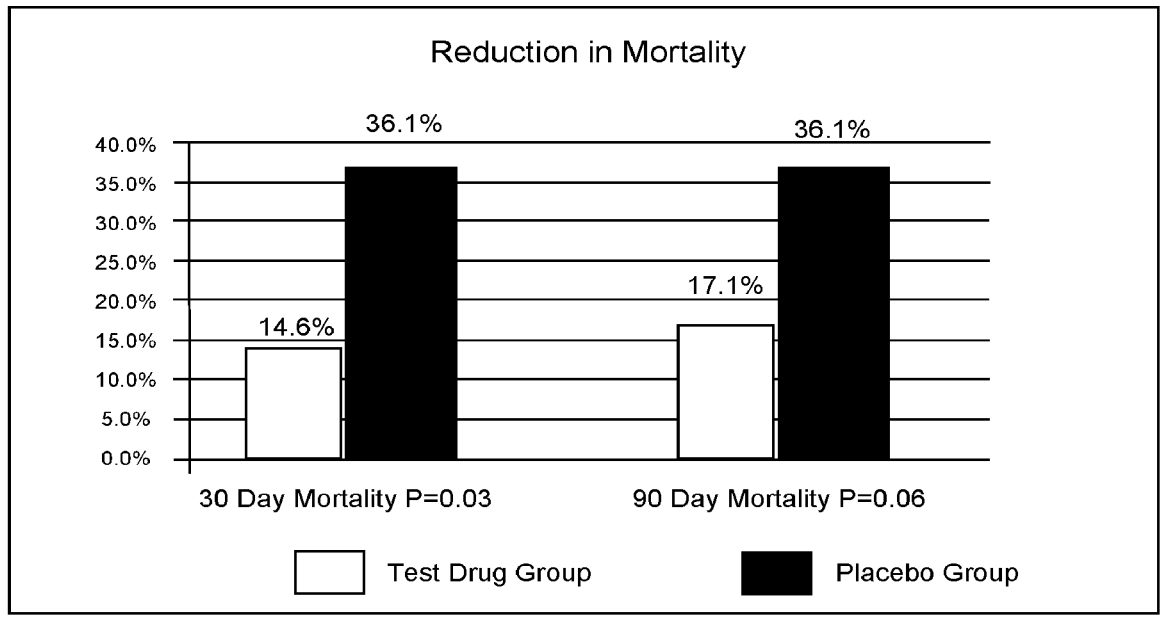
FIG. 1 shows the incidence rate of mortality in individuals that suffered an injury or condition related to cerebral edema in accordance with a clinical study that was conducted and is presented herein.

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

The singular forms "a," "an," and "the" include plural referents unless the context clearly dictates otherwise. Thus, for example, reference to "a SUR1-TRPM4 channel inhibitor" includes reference to one or more of such SUR1-TRPM4 channel inhibitors.

As used herein, the term "active agent" indicates a compound or mixture of compounds that when added to a composition, tend to produce a particular therapeutic effect.

As used herein, the term "Large Hemispheric Infarction" or "LHI" refers to an ischemic stroke affecting the total or sub-total territory of the middle cerebral artery (MCA), with or without involvement of the adjacent (e.g., anterior cerebral artery [ACA] and/or posterior cerebral artery [PCA]) territories.

As used herein, "late neurological deterioration" refers to neurological deterioration that occurs following an injury or condition that results in neurological swelling. The deterioration can occur at time periods that begin after the injury or condition occurs, but extend up to 72 hours, 96 hours, 120 hours, 144 hours, 168 hours, or more after the underlying injury or condition.

The term "lesion" refers to an abnormality in the tissue of the brain. In some instances, a lesion can be a space-occupying lesion that has recognizable volume and can impinge on nearby tissues and blood vessels.

As used herein, the term "placebo" is a formulation that does not contain a SUR1-TRPM4 antagonist, or is compositionally similar with the exception that the amounts (wt %) of a SUR1-TRPM4 channel inhibitor is replaced with the same amount (wt %) of other inert ingredients, e.g., water. Additionally, the "placebo" may have slight formulation differences that are typical due to the absence of the drug, as understood by those in the art.

The term "subject" as used herein includes all members of the animal kingdom, including mammals, and most typically, refers to human patients.

The term "sulfonylureas" includes sulfonylureas, sulfonylurea mimetics, and any other composition that is effective to block or reduce activity associated with the channels of SUR1.

The term "CNS edema" or "central nervous system edema" refers to swelling that can occur anywhere in the central nervous system, including at or near the brain or at or near the spinal cord. Thus, "spinal cord edema" and "cerebral edema" are two specific types of CNS edema, one of which impacts the spinal cord and the other which impacts the brain, respectively.

The phrases "injury or condition" that "relates to CNS edema" or "relates to cerebral edema" or "relates to the spinal cord" refers to the triggering event that can initiate or contribute to edema, e.g., CNS edema such as cerebral edema or spinal cord edema. It is noted, however, that these injuries or conditions do not always cause edema with every patient. For example, stroke is a condition that is related to CNS edema generally, and more specifically, related to cerebral edema. Stroke, in certain more severe cases, can lead to life threatening cerebral edema. Thus, stroke is condition that is related to CNS edema or cerebral edema in that there is risk of cerebral edema associated with stroke. In some specific examples, injuries or conditions that relate to cerebral edema can include ischemic stroke, hemorrhagic stroke, traumatic brain injury, cardiac arrest, liver failure, intraventricular hemorrhage, neurosurgery, or the like. Spinal cord injury, on the other hand, can be related to spinal cord edema. Some of these injuries or conditions are not directly associated with the brain or spinal cord, such as cardiac arrest or liver failure, but these injuries or conditions are known in some cases to lead to CNS or cerebral edema.

"Traumatic brain injury" refers to an injury that results in swelling in or around the brain, and which is related to mild, moderate, or severe injury that is typically direct to the area of the brain (e.g., impact injury at or near the head which can cause cerebral edema).

"Stroke" occurs when there is poor blood flow to the brain, and can result in cellular death. As defined herein, there are essentially two known types of strokes, namely ischemic stroke or hemorrhagic stroke. Ischemic stroke occurs when there is a lack of blood flow to the brain, and hemorrhagic stroke occurs when there is bleeding in the cranial vault or when there is bleeding within the brain tissue and includes subarachnoid hemorrhage and intracerebral hemorrhage. Both forms can lead to cerebral edema.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilizing (i.e. not worsening) the state of disease, delaying or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. In addition to being useful as methods of treatment, the methods described herein may be useful for the prevention or prophylaxis of disease.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. For example, in one embodiment, the degree of flexibility can be within about ±10% of the numerical value. In another embodiment, the degree of flexibility can be within about ±5% of the numerical value. In a further embodiment, the degree of flexibility can be within about ±2%, ±1%, or ±0.05%, of the numerical value.

Generally herein, the term "or" includes "and/or."

As used herein, a plurality of active agents, compounds, injuries or conditions, etc., may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0" should be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described. Additionally, it is noted that all percentages are in weight, unless specified otherwise.

As used herein, all percent compositions are given as weight-percentages, unless otherwise stated. When solutions of components are referred to, percentages refer to weight-percentages of the composition including solvent (e.g., water) unless otherwise indicated.

In understanding the scope of the present disclosure, the terms "including" or "comprising" and their derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps. It is understood that reference to any one of these transition terms (i.e. "comprising," "consisting," or "consisting essentially") provides direct support for replacement to any of the other transition term not specifically used. For example, amending a term from "comprising" to "consisting essentially of" would find direct support due to this definition.

As used herein, a plurality of compounds or steps may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Furthermore, certain compositions, injuries or conditions, steps, or the like may be discussed in the context of one specific embodiment. It is understood that this is merely for convenience, and such disclosure is equally applicable to other embodiments found herein. For example, a list of active agents or drugs described with respect to a method of treating late neurological deterioration or death would find direct support for embodiments related to methods of reducing cerebral midline shift, even if those drugs are not re-listed in the context of that embodiment in the specification.

In one embodiment, a method of reducing late neurological deterioration or death of a subject following an injury or condition related to CNS edema is presented. The method includes administering one or more continuous infusion of a SUR1-TRPM4 channel inhibitor to the subject for a cumulatively for at least about 72 hours after starting the continuous infusion(s). It has been found that administering the SUR1-TRPM4 channel inhibitor can reduce the incident of late neurological deterioration or death. Though this method relates to a subject, generally the incidence of late neurological deterioration or death can be determined based on a comparison to the incidence of late neurological deterioration in a group of patients that were not treated with the SUR1-TRPM4 channel inhibitor. "Late neurological deterioration" refers to neurological deterioration that occurs after extended time periods following the injury or condition related to CNS edema. Extended time periods can include ≥24 hours, hours, ≥≥72 hours, ≥84 hours, ≥96 hours, ≥108 hours, ≥120 hours, ≥132 hours, ≥148 hours, ≥160 hours, ≥172 hours, or about ≥184 hours.

SUR1-TRPM4 channel inhibitors can include any active agent that is effective for inhibiting SUR1-TRPM4, and some examples can include glyburide (also known as glibenclamide), 4-trans-hydroxy-glibenclamide, 3-cis-hydroxyglibenclamide, tobutamide, chlorpropamide, tolazamide, repaglinide, nateglinide, meglitinide, midaglizole, tolazamide, gliquidone, LY397364, LY389382, glyclazide, or glimepiride, metabolites that interact with SUR1, or combinations thereof. Some compounds that act on non-selective channels that may be associated with SURs include, for example, pinkolant, flufenamic acid, mefanamic acid, niflumic acid, rimonabant, and SKF 9635. In one embodiment, the SUR1-TRMP4 channel inhibitor is glyburide. In another embodiment, the SUR1-TRMP4 channel inhibitor is tobutamide. In yet another embodiment, the SUR1-TRMP4 channel inhibitor is glycazide.

The SUR1-TRPM4 channel inhibitor can be administered as a bolus injection, a continuous infusion, or a combination thereof. In some instances, the administration can include multiple bolus injections or multiple continuous infusions. In other embodiments, the administration can include one or more continuous infusion after a bolus injection. For example, a bolus injection can be given, followed by a first continuous infusion, followed by a second continuous infusion of a lower infusion rate compared to the first infusion. In another embodiment, a bolus injection is followed by a continuous infusion. In another embodiment, a first continuous infusion is followed by a bolus injection and then by a second continuous infusion. In yet another embodiment, a first continuous infusion is followed by a second continuous infusion, and a third continuous infusion.

The administration presented herein can occur over prolonged time periods. The administration can occur for hours, ≥24 hours, ≥48 hours, ≥72 hours, ≥76 hours, ≥80 hours, ≥84 hours, ≥88 hours, ≥92 hours, ≥96 hours, ≥100 hours, ≥104 hours, ≥108 hours, ≥112 hours, ≥116 hours, ≥120 hours, ≥0.124 hours, ≥0.128 hours, ≥132 hours, ≥136 hours, ≥140 hours, ≥144 hours, ≥148 hours, ≥152 hours, ≥156 hours, ≥160 hours, ≥164 hours, ≥168 hours, or ≥172 hours. In one embodiment, the administration includes one or more continuous infusion for cumulative length of time of at least 72 hours. In another embodiment, the administration includes one or more continuous infusion for at least 96 hours. In yet another embodiment, the administration includes one or more continuous infusion for at least 120 hours. In alternative examples, the administration of the one or more continuous infusion can occur for ≥72 hours, ≥48 hours, or ≥24 hours.

The exact dosage will vary based on the underlying condition, the extent of swelling, the subject's body weight, and/or the SUR1-TRMP4 channel inhibitor that is administered. Bolus injections are anticipated to be administered from about 100 μg to about 200 μg. In one embodiment, the bolus injection is from about 110 μg to about 140 μg, or about 125 μg. In another embodiment, the bolus injection is from about 140 μg to about 160 μg, or about 150 μg. In yet another embodiment, the bolus injection is from about 160 μg to about 190 μg, or about 175 μg. Continuous infusions are anticipated to be administration at an infusion rate from about 100 μg/hr to about 300 μg/hr. In one embodiment, the infusion rate is from about 110 μg/hr to about 140 μg/hr, or about 125 μg/hr. In another embodiment, the infusion rate is from about 140 μg/hr to about 160 μg/hr, or about 150 μg/hr. In yet another embodiment, the infusion rate is from about 160 μg/hr to about 190 μg/hr, or about 175 μg/hr. In further embodiments, the infusion rate is from about 190 μg/hr to about 225 μg/hr, or about 200 μg/hr. Additional embodiments include an infusion rate from about 225 μg/hr to about 300 μg/hr, or about 250 μg/hr.

Unlike clot busters that are typically administered to subjects with ischemic stroke, SUR1-TRPM4 channel inhibitors do not result in bleeding. Therefore, SUR1-TRPM4 channel inhibitors can be effective both when they are first administered quickly after the injury or condition, or some time period after the injury or condition that relates to cerebral edema occurs. In one embodiment, the first administration of the SUR1-TRPM4 channel inhibitor can be within the first hour, first 2 hours, first 3 hours, first four 4 hours, first 6 hours, first 8 hours, or first 10 hours of the injury or condition occurring. In another embodiment, the first administration of the SUR1-TRPM4 channel inhibitor can be at a time period after the injury or condition related to cerebral edema occurs of at least 4 hours, at least than 4½ hours (the time period at which clot busters can be ineffective or even dangerous), at least 6 hours, at least 8 hours, or at least 10 hours. In other examples, the first administration of the SUR1-TRPM4 channel inhibitor can be at a time period within 6 hours after the injury or condition occurs. In further embodiments, the first administration of the SUR1-TRPM4 channel inhibitor can be at a time period after 6 hours of the injury or condition occurring. In another embodiment, the first administration can be within 8 hours of the injury or condition occurring. In additional embodiments, the first administration of the SUR1-TRPM4 channel inhibitor can be at a time period within 10 hours of the injury or condition occurring.

The underlying injury or condition resulting in late neurological deterioration, death, or other condition discussed herein, is not particularly limited. It can include any disease or condition that results in cerebral swelling. In one embodiment, the underlying condition is traumatic brain injury. In another embodiment, the underlying condition is stroke. When the underlying condition is stroke, the stroke can be an ischemic or a hemorrhagic stroke. In another embodiment, the stroke can be ischemic stroke and occurs at the middle cerebral artery or carotid artery (intracranial or extracranial) or any other location related to ischemic stroke. When the stroke is a hemorrhagic stroke, it can occur or originate in any know location related to hemorrhagic stroke, including both or either a subarachnoid hemorrhage or an intracerebral hemorrhage.

Also presented herein is a method of reducing cerebral midline shift in a subject following a traumatic brain injury or a stroke. Cerebral midline shift can be caused by changes in lesion volume or lesional swelling. The method can include administering to a subject a SUR1-TRPM4 channel inhibitor following the subject experiencing the injury or condition related to cerebral edema, and performing a decompressive craniectomy on the subject. Midline shift can be measured on CT scans or MRI scans or using transcranial Doppler. The reduction in midline shift can be determined by a comparison with the amount of midline shift in stroke or TBI patients that were not treated with the SUR1-TRMP4 channel inhibitor or decompressive craniectomy. The reduction in cerebral midline shift can be greater than about 5%, greater than about 8%, greater than about 10%, greater than about 15%, greater than about 20%, greater than about 25%, greater than about 30%, greater than about 35%, greater than less than about 40%, greater than about 45%, or greater than about 50%. In some embodiments, the reduction in cerebral midline shift is greater than the reduction when either of a SUR1-TRPM4 channel inhibitor is administered or a decompressive craniectomy is performed. In other embodiments, the reduction is greater than the additive effect of either treatment conducted individually. In one embodiment, the SUR1-TRPM4 channel inhibitor reduced both lesion volume and lesional swelling. In another embodiment, the inhibitor of the SUR1-TRPM4 channel not only reduces cerebral midline shift but also treats lesional swelling. In some examples, the method can further include administering a tissue plasminogen activator (TPA) or clot buster active agent before, or along with the SUR1-TRPM4 channel inhibitor. This can be particularly effective when the TPA or clot buster active agent is administered while still considered safe, e.g., within the first 4½ hours of the injury or condition related to cerebral edema occurring. Examples of TPAs or clot buster active agents that can be co-administered can include activase, tenecteplase, eurokinase, streptokinase, and/or desmoteplase. Additionally, the clot can be removed by a device i.e. mechanical thrombectomy. The administration of the TPA or clot buster active agent is typically by intravenous infusion, but oral administration and subcutaneous administration are also included as routes of administration. The SUR1-TRPM4 channel inhibitor, administration type, administration rate, administration time frame, administration time period for the first dose, underlying conditions, other details, etc., can be as discussed above.

Further, the present disclosure is drawn to a method of improving a degree of disability in a subject that has suffered from an injury or condition related to CNS edema. The method includes administering one or more continuous infusion of a SUR1-TRPM4 channel inhibitor to a subject following the subject suffering from an injury or condition related to CNS edema. Additional steps include establishing an initial degree of disability for the subject based on a first scoring system or test, and determining a second degree of disability after a period of time from when initial degree of disability was determined using a second scoring system or test. In one example, the first and second scoring system or test can be the same, or alternatively, can be different. In this example, an improvement in a subject as determined, e.g., quantified, by the scoring system(s). In one example of this method, as a result of the SUR1-TRPM4 channel inhibitor administration, an improved difference in degree of disability is realized based on the scoring system or systems. For example, an improved difference in degree of disability can be realized that is at least about 10% based on the stroke scoring system(s). In other embodiments, the reduction of the degree of disability can be at least about 15%, at least about 20%, at least about 25%, or at least about 30%. The scoring system, particularly if the injury or condition related to CNS edema is a stroke, can be based upon a National Institutes of Health stroke score system (NIHSS), a modified Rankin Scale, a Barthel Index, or the size of the lesion as measured on CT and/or MRI. In one example, the first scoring system or test might be based on the NIHSS, and the second scoring system or test can be based on the modified Rankin Scale or the Barthel Index or the NIHSS. Imaging and/or other scoring systems can be used for other injuries or conditions related to CNS edema.

In another example, a method of treating a subject suffering from a large hemispheric infarction can include administering to the subject a therapeutically effective amount of an intravenous SUR1-TRPM4 channel inhibitor. In one example, the subject can be less than 71 years of age and the treating can result in improved functional outcomes as measured by one or more outcomes scales. In another example, the subject can have a lesion volume of at least about 100 cc, or an ASPECTS score of less than or equal to 5, or both. In another example, the administering can be initiated in 9 hours or less from the time of the index stroke or when the subject was last observed as normal. In still another example, the subject, prior to treatment, can show radiological evidence of intracerebral blood induced by the traumatic brain injury. Radiological evidence can be obtained using MRI or CT. The intracerebral blood can be due to a focal contusion with a minimum volume of at least about 0.5 mLs or at least about 1 mL, for example.

In another example, a method of testing a treatment for large hemispheric infarction can include enrolling subjects at least 18 years old with radiologically defined LHI; treating the subjects with a SUR1-TRPM4 channel inhibitor or matching placebo for up to about 72 hours, beginning 9 hours or less from the stroke or the last time observed normal; and assessing the mRS. The method can be considered successful if a statistically significant result favoring drug is detected in subjects 70-years old or younger, or a descriptive benefit is detected in subjects greater than 70-years old.

The SUR1-TRPM4 channel inhibitor, administration type, administration rate, administration time frame, administration time period for the first dose, underlying conditions, other details, etc., can be as discussed above and elsewhere herein.

In another embodiment, a method of counteracting a decline in blood glucose levels in a subject that is receiving a SUR1-TRPM4 channel inhibitor can include administering one or more continuous infusion of the SUR1-TRPM4 channel inhibitor to the subject, and co-administering a dextrose solution to the subject. An additional step can include measuring blood glucose levels before or during such administration. In one example, administration can be following or as a result of an injury or condition related to CNS edema. In another example, such a method can also be for administration of the SUR1-TRPM4 channel inhibitor for indications other than those related to CNS edema. In either case, this can be done to protect kidney, liver, intestines, or heart.

In one embodiment, the dextrose solution is administered initially if the blood glucose level of the subject is about 100 mg/dL or less. In another embodiment, the dextrose solution is administered initially if the blood glucose level in the subject is about 95 mg/dL or less. In yet another embodiment, the dextrose solution is administered initially if the blood glucose levels in the subject are about 90 mg/dL or less. In yet another embodiment, the dextrose solution is administered initially if the blood glucose levels in the subject are about 80 mg/dL or less. In a further embodiment, the dextrose solution is administered initially if the blood glucose levels in the subject are about 110 mg/dL or less. In a further embodiment, the dextrose solution is administered initially if the blood glucose levels in the subject are about 120 mg/dL or less. In yet another embodiment, a dextrose solution is administered if there is a rapid downward trend in the subject's blood glucose levels. Generally, if blood glucose is greater than about 140 mg/dL, dextrose supplementation should not typically be performed. A rapid downward trend would be defined by the clinician, but could include a reduction of ≥10 mg/dL, ≥20 mg/dL, ≥30 mg/dL, ≥40 mg/dL, ≥50 mg/dL, ≥60 mg/dL, ≥70 mg/dL, ≥80 mg/dL, ≥90 mg/dL, or ≥100 mg/dL since the last measurement.

The dextrose solution can be included of dextrose in saline or in water. The weight percentage of the dextrose in the dextrose solution typically be from 1 wt % to 25 wt %, though concentrations outside of this range can also be used, e.g., 2 wt % to 20 wt %, 3 wt % to 15 wt %, 3 wt % to 12 wt %, 3 wt % to 8 wt %, 8 wt % to 12 wt %, etc. In other words, the weight percentage of the dextrose in the dextrose solution can vary and can be administered to the subject based on certain variables, including the subject's blood glucose levels. Exemplary dextrose solutions such as these that are commonly used can include 5 wt % dextrose in normal saline (D5NS) and 10 wt % dextrose in normal saline (D10NS), but such solutions may also be in water or some fraction the normal saline (e.g., ½ normal saline) rather than normal saline. In one embodiment, when the subject's blood glucose level is from greater than about 80 mg/dL to 100 mg/dL, a 3 wt % to 8 wt % solution of dextrose can be administered to the subject at from about 50 cc/hr to about 120 cc/hr. In another embodiment, when the subject's blood glucose level is from about 55 mg/dL to 80 mg/dL, an 8 wt % to 12 wt % solution of dextrose can be administered to the subject at from 50 cc/hr to 120 cc/hr. In yet another embodiment, when the subject's blood glucose level is <55 mg/dL, an 8 wt % to 12 wt % solution of dextrose can be administered to the subject at from 50 cc/hr to 120 cc/hr. In a further embodiment, when the subject's blood glucose level falls below 55 mg/dL, administering of the glyburide or other SUR1-TRPM4 channel inhibitor is reduced or even ceased completely. In some embodiments, if a subject's blood glucose level drops below a certain level, such as 70 ml/dL, the method further includes administering a bolus of dextrose solution to the subject. In one embodiment, the bolus can be a 5 wt % to 60 wt % dextrose solution in water or saline and may specifically be 50% dextrose in water (D50W), ½ normal saline, or normal saline.

When determining the amount of dextrose to deliver, the practitioner can consider to the total fluids that be appropriately delivered to the subject (which can include maintenance fluids and the fluid containing the SUR1-TRPM4 channel inhibitor. In one example, the total fluid volume can be from 50 cc/hr to 200 cc/hr, or from 70 cc/hr to 150 cc/hr, or from 80 cc/hr to 130 cc/hr, for example. The exact volume can depend on clinical judgment, and should take into account any history of pulmonary edema. Using the Holliday-Segar nomogram, a typical total fluid rate for a 70 kg individual is 100 cc/hr, and for a 100 kg individual, 130 cc/hr.

In some embodiments, the method further includes monitoring of the subject's blood glucose levels. The monitoring can occur hourly, every 2 hours, every 4 hours, every 8 hours, every 12 hours, every 24 hours, or a combination thereof. In one specific embodiment, monitoring can be hourly for the first 24 hours that the SUR1-TRPM4 channel inhibitor is administered, then the monitoring will be every 2 hours for the next 24 hour hours, e.g., between hour 25 to hour 48, that the SUR1-TRPM4 channel inhibitor is administered, and then the monitoring can occur every 4 hours for the remainder of the R1-TRPM4 channel inhibitor infusion. If the subject's blood glucose levels drop below 70 mg/dL, monitoring can occur every 15 minutes until the subject's blood glucose level rises to ≥80 mg/dL for 3 consecutive readings without an exogenous bolus glucose administration, for example.

In some instances, high blood glucose levels may lead a decision to stop the dextrose solution to stop being administered. In this example, the dextrose solution can be stopped when the subject's blood glucose level is ≥150 mg/dL, about ≥140 mg/dL, about ≥130 mg/dL, or about ≥120 mg/dL. In one instance, all blood glucoses of <≥70 mg/dL may be verified either by performing another measurement at the bedside, or by laboratory test, prior to stopping or reducing the administration of the drug.

In one embodiment, subjects treated with a SUR1-TRPM4 inhibitor can be monitored for blood glucose, by way of one example, as follows:
Hourly (±30 min) for about the first 24 hours;
Every 2 hrs (±30 min) for hours about 25 to about 48; and
Every 4 hrs (±60 min) thereafter.
When blood glucose falls to less than about 70 mg/dL, monitoring frequency can be increased to every 15 min (±10 min) until the blood glucose is greater than or equal to about 80 for about 3 consecutive readings without exogenous glucose supplementation.

If drug is interrupted and resumed, blood glucose can be measured hourly for about 3 hrs (±30 min).

If no glucose is required, monitoring can be resumed to the previous protocol frequency, e.g., 1, 2, or 4 hrs in this example.

In another embodiment, blood glucose can be controlled in subjects treated with a SUR1-TRPM4 inhibitor, by way of example, as follows:
If the blood glucose at baseline is less than about 100 mg/dL, the initial maintenance fluid may be about 5% dextrose in normal saline (D5NS) at a rate of about 70 to about 100 cc/hr.
If blood glucose falls below about 100 mg/dL, D5NS can be started at about 70 to about 100 cc/hr. Titration of the IV fluid rate up or down can be used to maintain blood glucose above about 80 mg/dL.
If blood glucose is less than about 80 mg/dL, D5NS can be started or, if D5NS is already being administered, then the subject can be switched to about a 10% dextrose in normal saline (D10NS).
If there is a rapid or continuous downward trend in blood glucose, then D5NS can be started, or if D5NS is already being administered, then the subject can be switched to D10NS.
In the event of blood glucose greater than about 140 mg/dL, D5NS or D10NS can be not administered.
Any confirmed blood glucose of less than about 70 mg/dL can be treated with a 50 mL ampule of about dextrose 50% in water (D50W). If D50W is not available, another concentration of dextrose fluid can be used at a sufficient volume to achieve an equivalent amount of dextrose.

The SUR1-TRPM4 channel inhibitor, administration type, administration rate, administration time frame, administration time period for the first dose, underlying conditions, other details, etc., can be as discussed above and elsewhere herein, or can be modified according to clinical decisions made by the medical professional managing the treatment, for example. For example, different dosages and timings can carried out, or different routes of administration can also be carried out.

In another example, a method of preventing brain swelling in a subject at a high risk for severe brain swelling can include determining whether the subject is at a high risk for severe brain swelling, and administering one or more continuous infusion of a SUR1-TRMP4 channel inhibitor to the subject once determined to be at high risk for severe brain swelling.

To illustrate stroke as an example where this method would provide benefits, it is generally accepted that life threatening swelling can occur in up to 8% of hospitalized ischemic stroke patients and up to 15% of all middle cerebral artery (MCA) strokes. Patients that progress to such swelling present with a National Institute of Heath Stroke Score (NIHSS) typically greater than 20 when the dominant hemisphere is involved, and greater than 15 when the nondominant hemisphere is involved. In other examples, most (perhaps more than 99%) of cases that go on to develop significant swelling have an NIHSS 10. Patients under an NIHSS score of 10 do not tend to develop life threatening swelling. Thus, subjects at high risk for developing such swelling can be identified using imaging or scoring techniques. Accordingly, with stroke or other injury or condition related to cerebral edema, a subject may be considered to be at a high risk for severe brain swelling when the subject exhibits at least one factor selected from the group consisting of: a National Institutes of Health Stroke Scale (NIHSS) score of at least 10; a Alberta Stroke Program Early CT Score (ASPECTS) of 7 or less; a Alberta Stroke Program Early CT Score (ASPECTS) of 4 or less; a magnetic resonance imaging (MRI) diffusion weighted image (DWI) of greater than 70 cc; a magnetic resonance imaging (MRI) diffusion weighted image (DWI) of greater than 82 cc; a magnetic resonance imaging (MRI) diffusion weighted image (DWI) of greater than 145 cc; a CT perfusion core that is greater than 50 cc; a CT perfusion core that is greater than 70 cc; poor collateral circulation determined by CT angiography (or other means); a CT scan that shows a hypodensity covering at least 33% of the middle cerebral artery territory; and/or a CT scan that shows a hypodensity covering at least 50% of the middle cerebral artery territory. In some embodiments, the subject is first assessed to have an NIHSS of 10 or greater, and then assessed by one of the other methods outlined above. In some embodiments, the subject can be considered at a high risk when the ASPECTS score ≤5, ≤4, ≤3, or ≤2. In some embodiments the subject is considered to be at a high risk when the MRI DWI is greater than 82 cc.

In particular, patients suffering from a Large Hemispheric Infarction (LHI) are especially at risk of swelling. These subjects typically have a middle cerebral artery territory stroke and can be further identified radiologically using MRI, DWI, or CT perfusion of at least about 70 cc, at least about 80 cc, at least about 90 cc, or at least about 100 cc, or exhibit an ASPECTS score of ≤5, ≤4, ≤3, or ≤2. In methods contemplated herein of treating subjects with LHI, in one example, subjects can be less than about 76 years old or less than about 71 years. Additionally, subjects having an National Institutes of Health Stroke Scale (NIHSS) of at least 10 where the drug was administered in 10 hours or less from the index stroke or last known incident time can have acceptable results. An administration time of 9 hours or less can also provide acceptable result. These methods can result in improvements on one or more clinically relevant endpoints, including: survival/mortality, the modified Rankin Scale (as a full ordinal scale and/or dichotomized); the Barthel Index; and/or the EuroQol. These improvements can be manifest at one or more time points to include about 90 days (or about 3 months), about 180 days (or about six months), and/or about 12 months (or one year) following the stroke.

Related to the methods of treating LHI, methods of testing a drug to treat LHI are also contemplated. According to these methods, LHI patients of ages 18 and older can be selected radiologically and enrolled. Subjects tested can typically have an NIHSS of 10 or more and can be treated with a SUR1-TRPM4 channel inhibitor, or matching placebo, beginning within 10 or less hours of the stroke or last know incident time (or even at 9 or less hours), with treatment lasting for up to about 72 hours. These methods can result in improvements in the drug versus placebo groups on one or more clinically relevant endpoints, including: survival/mortality, the modified Rankin Scale (as a full ordinal scale and/or dichotomized); the Barthel Index; and/or the EuroQol. These assessments are made at one or more time points to include about 90 days (or about 3 months), about 180 days (or about six months), and/or about 12 months (or about one year) following the stroke.

Table 1, as follows, provides an exemplary dosing schedule. References to mass refers to the SUR1-TRPM4 channel inhibitor in the drug only (note that the placebo has none).

TABLE 1

Dosing Regimen

| | 0 to 24 Hours | | >24 to 48 Hours | >48 to 72 Hours |
|---|---|---|---|---|
| | Bolus | Infusion | Infusion | Infusion |
| Concentration | 5.3 µg/mL | 5.3 µg/mL | 5.3 µg/mL | 5.3 µg/mL |
| Dose | 0.13 mg | 2.99 mg | 2.67 mg | 2.67 mg |
| Total Volume | 24 mL | 564 mL | 504 mL | 504 mL |
| Dose/hr | 3.9 mg/hr | 0.16 mg/hr  0.11 mg/hr | 0.11 mg/hr | 0.11 mg/hr |
| Volume/hr | 720 mL/hr | 31 mL/hr  21 mL/hr | 21 mL/hr | 21 mL/hr |
| Duration | 2 min (±1 min) | 6 hrs (±5 min)  18 hrs (±5 min) | 24 hrs (±10 min) | 24 hrs (±10 min) |

In assessing the outcome, the subjects can be divided into two age groups: ≤70 years old and >70 years old. Statistical significance is assessed only in the ≤70-year old population on the mRS using an analysis that retains the ordinal scale, such as the Mann Whitney test (and similar tests), ordinal logistic regression under a proportional odds assumption, which provides a sliding dichotomy. Success is defined in terms of a two-sided p-value of <0.05 or an odds ratio where the 90% confidence interval does not cross 1. The population >70 is analyzed descriptively only, which may include describing a point estimate of a common odds ratio derived using ordinal logistic regression or one or more odds ratios based on individual points of dichotomization on the mRS (e.g., 0-4 v 5-6; 0-3 v 4-6; or 0-2 v 3-6). Survival/mortality is also assessed. Such odds ratio should favor drug treatment, but may be associated with 90% confidence intervals crossing 1. A similar point estimate can be employed in the 70 population to elucidate the direction and magnitude of any treatment effect demonstrated by the Mann Whitney test (or similar test). An odds ratio that is calculated should be greater than about 1.1, greater than about 1.2, and even more desirably, greater than 1.3 in favor of drug.

The SUR1-TRPM4 channel inhibitor, administration type, administration rate, administration time frame, administration time period for the first dose, underlying conditions, other details, etc., can be as discussed above and elsewhere herein.

Additionally, a method of safely delivering glyburide to a subject can include administering one or more continuous infusion of glyburide to the subject, and measuring liver enzyme levels while continuing administration of the glyburide. In one example, administration can be following or as a result of an injury or condition related to CNS edema. In another example, such a method can also be for administration of the glyburide for indications other than those related to CNS edema. In either case, this can be done to protect kidney, liver, intestines, or heart. According to the package insert for oral glyburide, glyburide may cause transient transaminase elevations.

In some instances, the method further includes the preliminary step of measuring the subject's liver enzyme levels prior to administering the glyburide. This can be done to establish a baseline liver enzyme level. The method can also include measuring liver enzyme levels at specified time periods after starting the administering step. In some embodiments, the subject's liver enzyme levels can be monitored at 4 hour intervals, 6 hour intervals, 8 hour intervals 12 hour intervals, 24 hour intervals, etc. Alternatively, levels can be checked at about 12 hours, about 24 hours, about 36 hours, about 48 hours, about 60 hours, about 72 hours, about 84 hours, about 96 hours, about 108 hours, about 120 hours, about 132 hours, about 154 hours, about 168 hours, the day the subject is discharged, or a combination thereof.

The monitoring can include measuring various enzymes. In one embodiment, the liver enzyme that is measured is aspartate transaminase (AST). In another embodiment, the liver enzyme that is measured is alanine transaminase (ALT). In another embodiment the liver enzyme is indirect, and/or direct, and/or total bilirubin. The monitoring can likewise involve measuring both the subject's AST and ALT values or ALT and bilirubin or ALT, AST and billirubin. In one embodiment, the administration of the glyburide is discontinued if the subject's ALT or AST level rises to greater than about 8 times an upper limit of normal ALT or AST levels. In one embodiment, the administration of the SUR1-TRPM4 channel inhibitor can be discontinued if the subject's ALT or AST level rises to greater than about 6 times an upper limit of normal ALT or AST levels as determined by an administering practitioner. In yet another embodiment, the administration of the glyburide is discontinued if the subject's ALT or AST level rises to greater than about 4 times an upper limit of normal ALT or AST levels as determined by an administering practitioner. In a further embodiment, the administration of the glyburide can be discontinued if the subject develops cholestatic jaundice or hepatitis. What these exact levels are and what constitutes an unsafe risk for continued treatment can be determined by the practitioner based on existing enzyme levels, levels considered to be safe, tradeoffs between enzyme levels vs. treating the CNS edema, etc. In one embodiment, the administration of the glyburide can be discontinued if the subject's total bilirubin level rises to greater than about 2 times an upper limit of normal.

The administration type, administration rate, administration time frame, administration time period for the first dose, underlying conditions, other details, etc., can be as discussed above and elsewhere herein.

In another example, a method of monitoring cardiac activity when a sulfonylurea agent is administered to a subject can include administering one or more continuous infusion of glyburide to the subject, and performing an electrocardiogram on the subject to monitor the subject's heart. In one example, administration can be following or as a result of an injury or condition related to CNS edema. In another example, such a method can also be for administration of the glyburide for indications other than those related to CNS edema. In either case, this can be done to protect kidney, liver, intestines, or heart. Sulfonylureas, including glyburide, carry a black box warning for cardiac mortality. In addition, a study of oral glyburide indicated that it may cause QTc prolongation.

In one embodiment, the method can further include performing the electrocardiogram on the subject prior to administering the glyburide or another sulfonylurea agent. In yet another embodiment, the step of performing the electrocardiogram includes performing electrocardiograms on the subject at specified time periods after starting the administering step. The specific time periods for performing the electrocardiogram can be from about 2 to 8 hours apart, about 4 to 6 hours apart, at about hour 4-6 (after starting the infusion), at about 24 hours, about 48 hours, about 60-72 hours, about 168 hours, the day the subject is discharged, or combination thereof. The method can include ceasing glyburide administration if the subject's QTc is ≥ about 550 ms, ≥ about 600 ms, ≥ about 500 ms, ≥ about 475 ms, or ≥ about 450 ms, such as for a period of at least about 10 minutes, at least about 15 minutes, or at least about 30 minutes. Repositioning of the leads can occur to ensure that the reading is accurate if desired.

The administration type, administration rate, administration time frame, administration time period for the first dose, underlying conditions, other details, etc., can be as discussed above and elsewhere herein.

In another example, a method delivering glyburide to a subject can include intravenously administering glyburide to the subject, and monitoring blood glucose, liver enzymes, and QTc during while intravenously administering the glyburide to the subject. Any of the embodiments described herein, along with the details associated therewith, can be applicable to this example.

Regarding the various methods discussed herein, as mentioned, they are applicable to a variety of injuries or conditions related to CNS edema. That being, said not all such injuries or conditions always lead to CNS edema, and thus, can be "related to" or stated another way "at risk" of causing CNS edema. One example of this is stroke. For example, space-occupying brain edema secondary to a hemispheric (involving the entire middle cerebral artery territory or more) ischemic stroke can lead to intracranial hypertension and eventual brain herniation, resulting in significant morbidity and mortality. This condition usually manifests itself between the second and the fifth day after ischemic stroke onset, with swelling peaking at two to three days after the incident. This can further lead to the destruction of formerly healthy brain tissue and to extensive brain tissue shifts resulting in transtentorial or uncal herniation and brain death, and thus, such complications can be responsible for the rapid neurologic deterioration seen in such patients. For example, life threatening swelling can occur in up to 8% of hospitalized ischemic stroke patients and up to 15% of all middle cerebral artery (MCA) strokes. Thus, whether it be from a stroke or other injury or condition related to CNS edema, the methods of the present disclosure can benefit many of such subjects that are experiencing or are at risk of experiencing CNS edema.

Embodiments of the present disclosure will be described with reference to the following Examples, which are provided for illustrative purposes only and should not be used to limit the scope of or construe the invention.

Example 1—Randomized Double Blind Placebo Controlled Study in Large Hemispheric Infarction In order to determine the efficacy of SUR1-TRPM4 channel inhibitors for reducing or treating neurological conditions associated with cell swelling and CNS or cerebral edema, a randomized double blind placebo controlled clinical study was conducted. In the clinical study, 83 subjects were estimated by clinicians to have brain lesions of 82 cc to 300 cc were treated within about ten hours of an injury or condition related to cerebral edema with either a test drug solution of glyburide or a placebo solution. Within the "per protocol" group, 77 patients who were confirmed centrally to have brain lesions from 82 cc to 300 cc. Forty one of subjects were administered the test drug and 36 subjects were administered the placebo. The administration of the test drug was as follows: a bolus of 0.13 mg of the SUR1-TRPM4 channel inhibitor was administered over approximately 2 minutes followed by a continuous infusion of 0.16 mg/hr for 6 hours, and then a continuous infusion of 0.11 mg/hr for 66 hours, for a total dosing period of 72 hours. The total daily dose of Study Drug on Day 1, Day 2 and Day 3 was 3.12 mg, 2.67 mg, and 2.67 mg, respectively.

Mortality Data

The incidence of mortality in the individuals was recorded at both 30 and 90 days following treatment. The Reduction in Mortality as a result of administration of the SUR1-TRPM4 channel inhibitor is shown in Table 2 below, and graphed in FIG. 1.

TABLE 2

Mortality Incidences

| Study Group | # Individuals in the Group | Mortality 30 days | % Death 30 days | Mortality 90 days (includes 30 day values) | % Death 90 days |
| --- | --- | --- | --- | --- | --- |
| Test Drug Group | 41 | 6 | 14.6% | 7 | 17.1% |
| Placebo Group | 36 | 13 | 36.1% | 13 | 36.1% |

As can be seen in the table above, subjects in the Test Drug Group had a lower percentage of death by about more than half.

Decompressive Craniectomy (DC) Data

Additional mortality data was collected as it related to drug and placebo treatment with and without a Decompressive Craniectomy (DC). Essentially, the incidence of mortality was recorded for study participants that passed away following a DC prior to the end of the study period. The incidence of mortality when a DC occurred compared to no DC is shown in Table 3 below, and graphed in FIG. 2.

TABLE 3

Mortality Incidences with and without Decompressive Craniectomy

| Study Group | # Individuals Receiving DC vs. No DC | Mortality with DC | Mortality without DC |
| --- | --- | --- | --- |
| Test Drug Group | 13 DC/28 no DC | 2 | 5 |
| Placebo Group | 28 DC/8 no DC | 11 | 2 |

Figure 2:
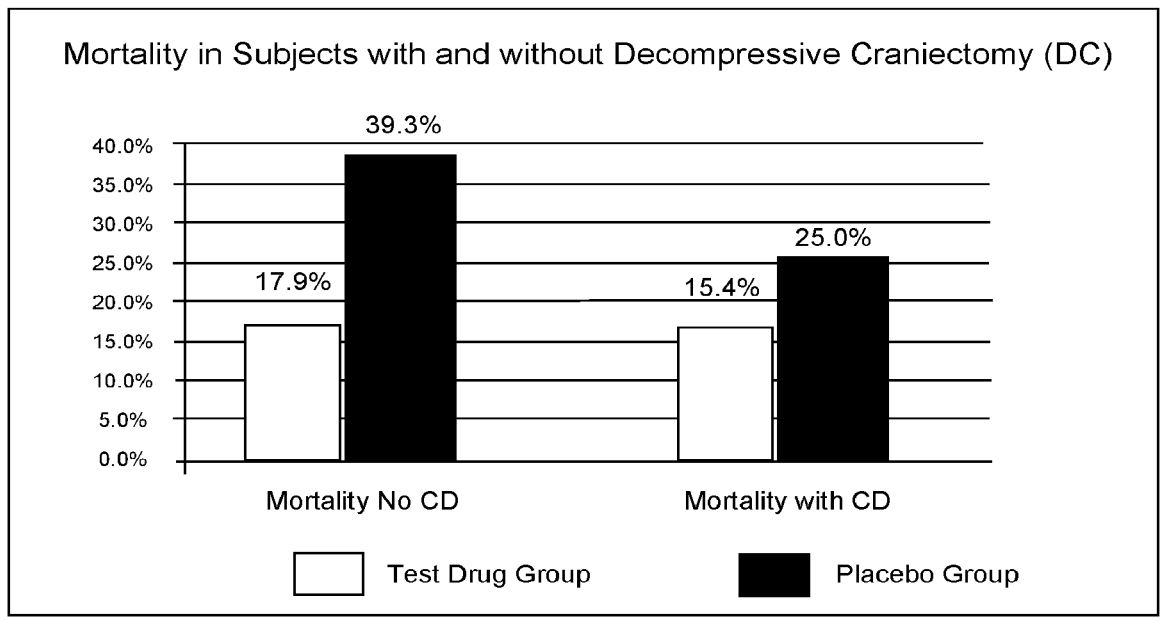
FIG. 2 shows the incidence rate of mortality in individuals that suffered an injury or condition related to cerebral edema and were treated with a decompressive craniectomy surgery and either the study drug or a placebo in a clinical study that was conducted and is presented herein.

As can be seen in Table 3, in this particular study, the best results were achieved with the Test Drug Group who also received a DC procedure, but those results are only marginally better than with the Test Drug Group that did not receive a DC procedure. In further detail, with the Placebo Group, though a DC procedure helped compared to not receiving a DC procedure, both were inferior to the outcomes found in the Test Drug Group (with or without a decompressive craniectomy surgery). FIG. 2 shows the raw values found Table 3 in terms of percentages. Note that the average time prior to decompression is not accounted for in these numbers as they are widely variable based on the judgment, and to some degree, schedule of the practitioner in charge of making these type of decisions. It is also noted that two late decompressive surgeries occurred due to late neurological deterioration. These surgeries might have been avoided if patients were treated with the SUR1-TRPM4 channel inhibitor for longer, for example 5 days or 7 days.

mRS Scores

Figure 3:
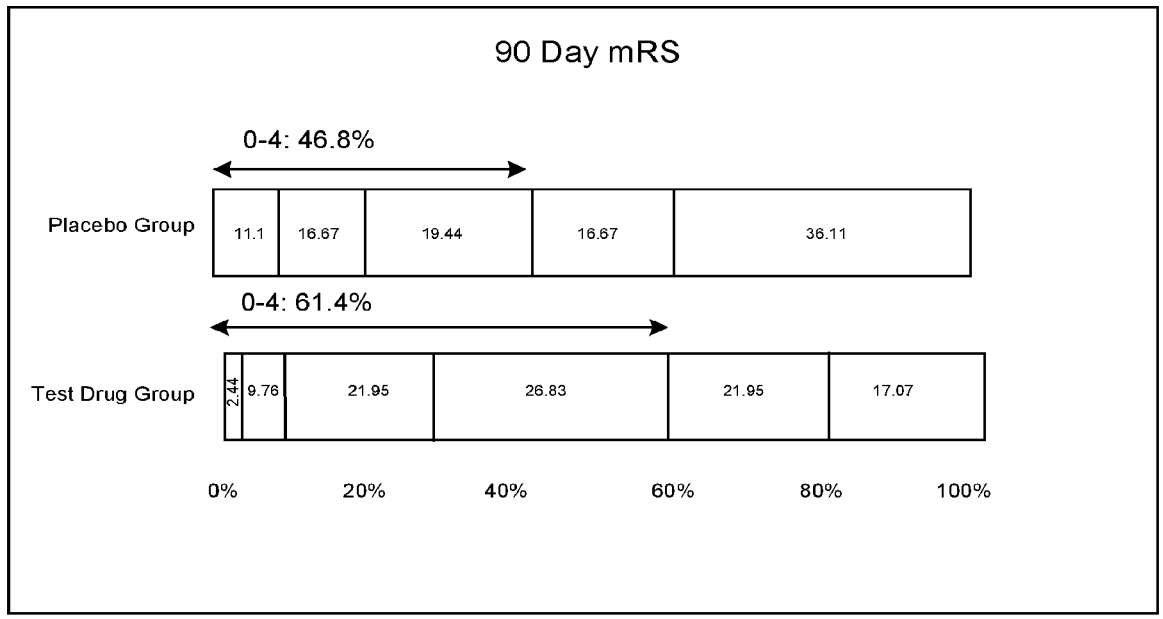
FIG. 3 shows the distribution of mRS scores for individuals in the clinical study.

The subjects in this study were also tested using the modified Rankin Scale (mRS). One way to assess outcome in large strokes, such as those studied, is to determine the percentage of patients in each group who have a mRS of 0-4 at 90 days after stroke. The results of the 90 day mRS study is shown in Table 4 below, and graphed in FIG. 3.

TABLE 4 mRS Scores

| Study Group | 90 Day Score of mRS 0-4 |
| --- | --- |
| Test Drug Group | 61.4% |
| Placebo Group | 46.8% |
| Difference | +14.6% |

As can be seen in Table 4, the proportion of mRS scores of 0-4 in subjects that received the SUR1-TRPM4 channel inhibitor was 14.6% more on average than the mRS scores of individuals that did not receive the study drug. Additionally the median mRS in the treated group was 4 vs. a median of 5 in the placebo.

Barthel Index

Figure 4:
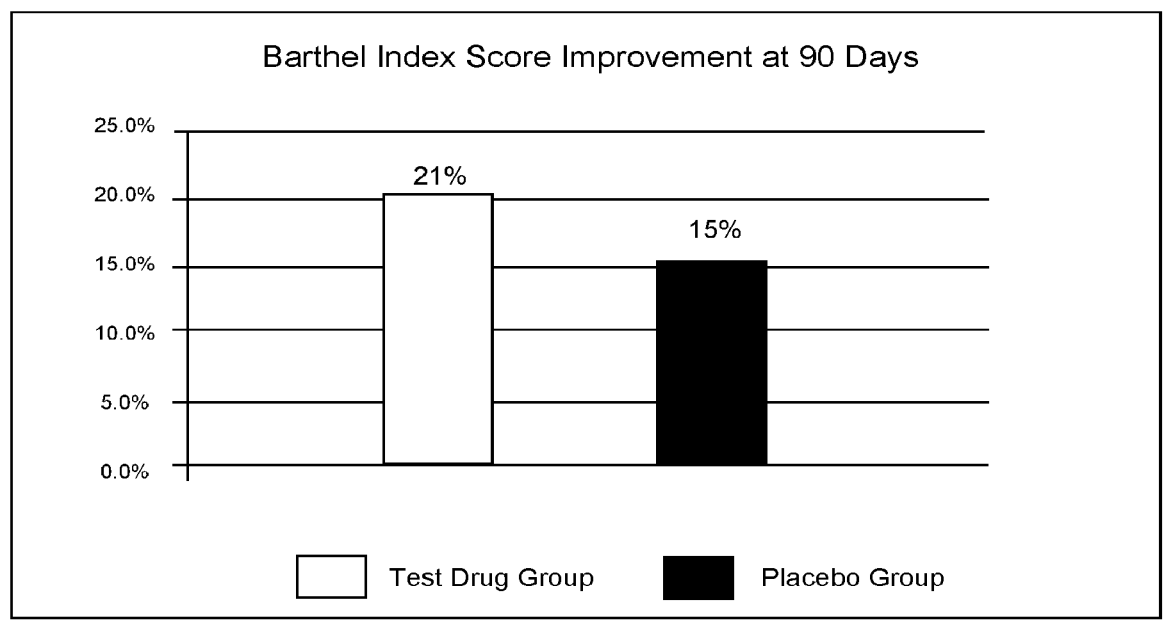
FIG. 4 shows the median 90 day Barthel Index Scores for individuals in the clinical study that was conducted and is presented herein.

The Barthel Index is another functional outcome that can be used to assess outcome of stroke patients. The subjects of the study were also scored using the Barthel index both initially and again at about 90 days. The degree of improvement in the Barthel index scores are shown in Table 5 below and graphed in FIG. 4.

TABLE 5

Barthel Index Score Improvement

| Study Group | Barthel Index |
|---|---|
| Test Drug Group | 21 |
| Placebo Group | 15 |

As can be seen in Table 5, Barthel Index Scores were better in the Test Drug Group than the Placebo Group.

Midline Shift Data

Figure 5:
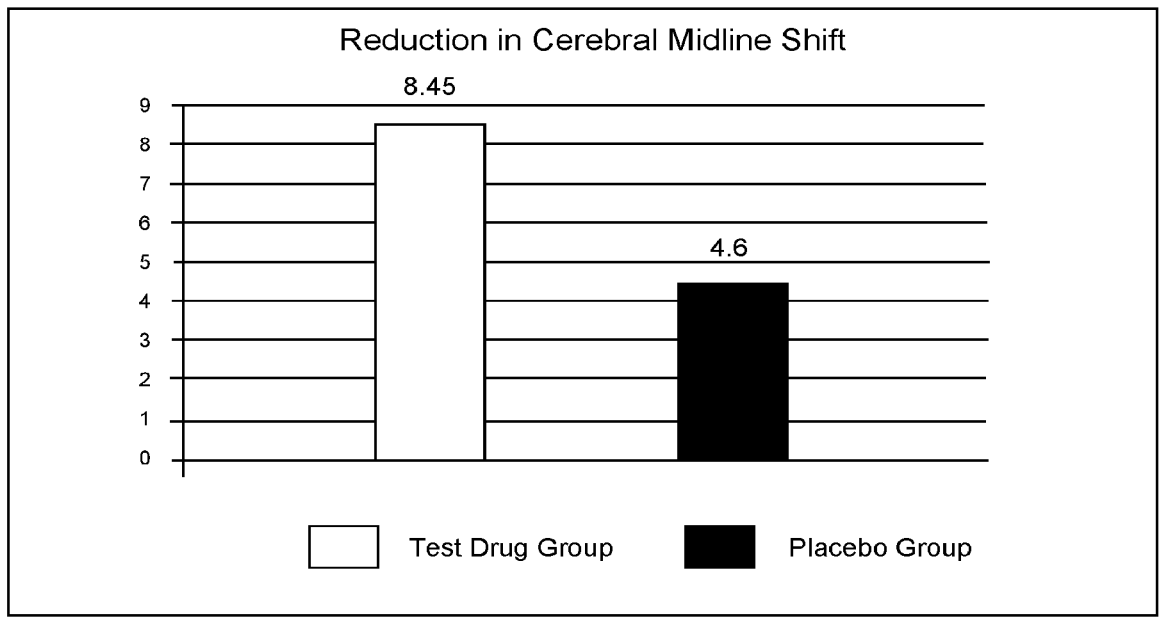
FIG. 5 shows the average percent reduction in cerebral midline shift for study participants.

The subjects of the study also underwent a MRI scan at 72-96 hours, and images were taken to observe the extent of the reduction in midline shift. The average percent reduction is shown in Table 6 below, and graphed in FIG. 5.

TABLE 6

Percent Reduction in Midline Shift

| Study Group | Median Midline Shift (mm) |
|---|---|
| Test Drug Group | 8.45 |
| Placebo Group | 4.6 |

Based on the MRI scan images, the percent reduction in midline shift (or greater reduction in midline shift) favored individuals on average within the Test Drug Group over the Placebo Group. Percent reduction was determined by comparing the median midline shift of each group at 72-96 hours.

FLAIR Ratio

Figure 6:
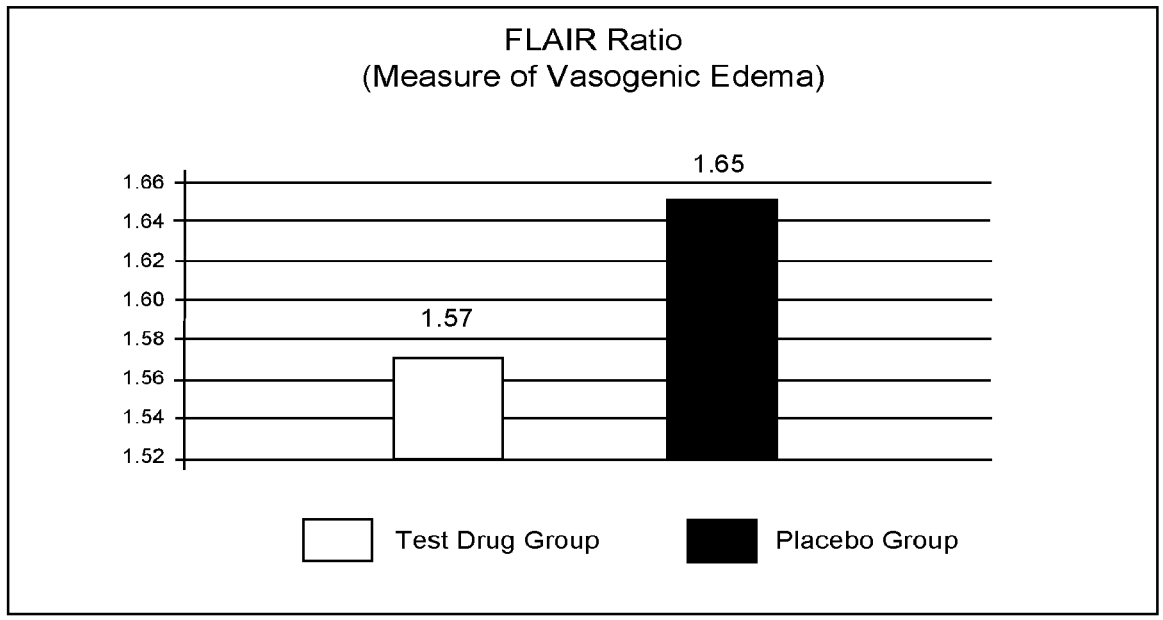
FIG. 6 shows the FLAIR ratio for individuals in the clinical study that was conducted and is presented herein.

A FLAIR Ratio (a MRI measure of disturbance of the blood brain barrier) study was also conducted, where study subjects, when possible, were evaluated to determine the reduction in vasogenic edema. The FLAIR ratio results are shown in Table 7 below, and graphed in FIG. 6.

TABLE 7

FLAIR Ratio

| Group | FLAIR Ratio |
|---|---|
| Test Drug Group | 1.57 |
| Placebo Group | 1.65 |

Based on this study, the Test Drug Group on average performed better than the Placebo Group. A lower FLAIR ratio is indicative of less disturbance of the blood brain barrier.

MMP Disruption

Figure 7:
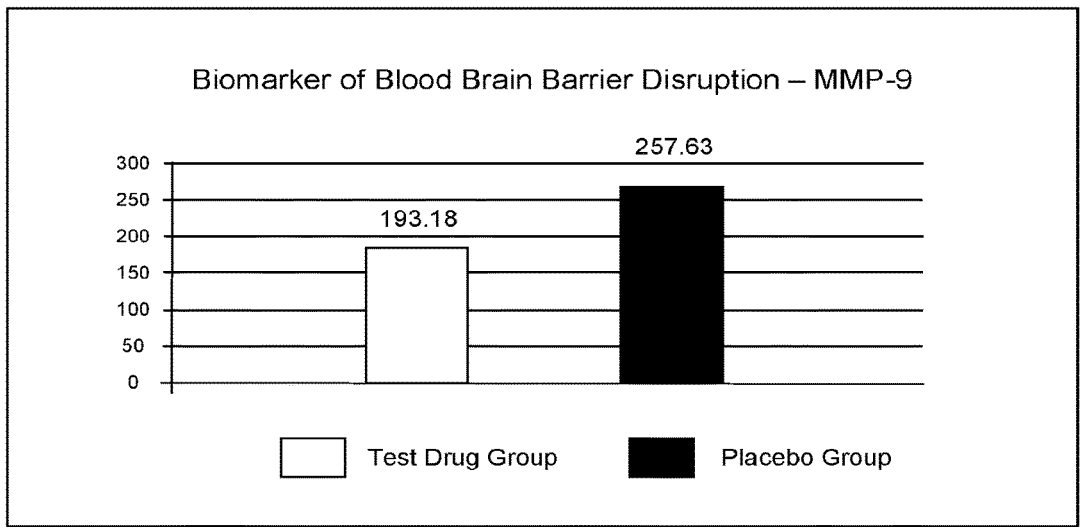
FIG. 7 shows and Blood Brain Barrier disruption for individuals in the clinical study that was conducted and presented herein.

Additionally, MMP-9 values based in blood samples were taken at 24 hours and at 72 hours for the study participants and then averaged. MMP-9 levels are known to rise after stroke and are believed to represent blood brain barrier dysfunction. The MMP-9 average values are shown in Table 8 below, and graphed in FIG. 7.

TABLE 8

MMP Disruption

| Group | Average (ng/mL) |
|---|---|
| Test Drug Group | 193.18 |
| Placebo Group | 257.63 |

Based on this study, the Test Drug Group on average performed better than the Placebo Group.

Blood Glucose Monitoring and Modification a) During the Double Blind Placebo Controlled Study, there was a lab confirmed blood glucose level that dropped to 51 mg/dL which was recorded for one of the patients who was receiving a 10 wt % dextrose solution. In this example, the dose of glyburide infusion rate was reduced by 30% and the patient's blood glucose level stabilized.

b) During the Double Blind Placebo Controlled Study, one of the patients had a blood glucose level of 57 mg/dL at the point of care, and was lab re-tested at 67 mg/dL. In this instance, the patient was on normal saline and then was moved to 5 wt % dextrose where the patient's blood glucose stabilized.

Results in Subjects 70 Years Old

In an effort to identify the population most likely to benefit from treatment, different age groups were analyzed and, despite the fact that ischemic stroke is understood to be a condition of the elderly, it was found that efficacy was surprisingly more pronounced in the population 70 years of age, which was consistent at multiple endpoints, including survival/mortality, mRS, the Barthel Index and the EuroQol-5D.

Improvements on Survival

In a full per-protocol population, while the odds ratio (OR) ranged from 2.54 to 2.74 at various time points. These results were just beyond statistical significance at Day 90 or later (an odds ratio of 1 indicated no effect), thus showing improvement generally across the board. However, in the 70 per-protocol population, results were statistically significant at all time points, with a more substantial OR range, ranging from 3.41 to 3.79. The data is shown below in Table 9.

TABLE 9

Comparison of the Survival Effects in the Full vs. the ≤70 Per-Protocol Population

| | Full Population | | ≤70 Population | |
|---|---|---|---|---|
| Time | OR | p-value | OR | p-value |
| Day 90 | 2.74 | 0.06 | 3.88 | 0.04 |
| 6 Months | 2.63 | 0.08 | 3.47 | 0.05 |
| 12 Months | 2.54 | 0.09 | 4.00 | 0.03 |

Mortality can be multifactorial and may depend on factors such as preexisting comorbidities and risk factors. To further understand the effect of glyburide, survival benefit attributable to our hypothesized mechanism of action was elucidated. Specifically, cause of death was adjudicated by three adjudicators blinded to study drug group. Imaging and clinical data were used to determine, among other outcomes, cause of death. Adjudicated mortality due to edema in the per-protocol group was found to be 2.44% (1/41) vs. 22.22% (8/36), and p=0.01 (Fisher's exact two-sided p). Consistent with our proposed mechanism of action, mortality attributable to edema was the driver behind reductions in overall mortality.

Improvements on the mRS

The mRS rates global disability following stroke and assessed at 90 days is the most widely used primary outcome measure commonly used in acute stroke trials. This measure provides an ordinal, hierarchical scale that rates disability on a scale from 0 (no symptoms) to 6 (death). Although the mRS has often been analyzed as a dichotomous outcome, this approach often diminishes the power to detect an effect and, in fact, has been found to obscure both positive and negative effects. In contrast, ordinal analysis can retain the full power of the mRS and better reflects health status by valuing each transition.

The magnitude of difference between placebo and treatment arms on the mRS as an ordinal scale is frequently measured using the Mann-Whitney test and a common odds ratio (OR) may be derived using the proportional odds methodology to explore effect size. In accordance with this, a common OR of 1.2 represents a clinically meaningful difference. The OR for effect size in patients ≤70 in the per-protocol population was 2.49, which represents a substantial clinical effect.

TABLE 10

Comparison of the Effects on mRS in the Full vs. the ≤70 Per-Protocol Population

| Time | Full Population | | ≤70 Population | |
|---|---|---|---|---|
| | OR | p-value | OR | p-value |
| Day 90 | 1.91 | 0.12 | 2.49 | 0.048 |
| 6 Months | 1.88 | 0.13 | 2.33 | 0.064 |
| 12 Months | 1.64 | 0.24 | 2.24 | 0.08 |

While less powerful statistically significant, the effect size at the 0-3 and 0-4 dichotomizations in the patients ≤70 in the per-protocol population were 14% and 22% respectively, well above the minimum clinically relevant effect sizes and demonstrating a substantial clinical effect on the mRS.

Improvements on the BI

The Barthel Index (BI) is a measure of activities of daily living. It has been widely used and accepted in stroke trials and is one of the more prevalent scales used in acute stroke. In one example, a minimum clinically important change that is beyond measurement error is about 20 points on the 100-point scale, which was used as a benchmark in this study. The median delta or differences seen in the ≤70 per-protocol population at 90 days, 6 months, and 12 months between drug and placebo were 35, 27.5, and 45, respectively, all exceeding the accepted threshold. A common interpretation of the BI considers a score of ≤40 to be a clearly bad outcome, whereas a score of ≥60 is a clearly good outcome. In this trial, the median BI scores in the placebo group were ≤40 at 90 days, 6 months, and 12 months (25, 32.5 and 30, respectively), whereas in the glyburide group, the score was ≥60 at all time points (60, 60, and 75, respectively). These results at 12 months were also statistically significant (p=0.03).

TABLE 11

Comparison of the Effects on the BI in the Full vs. the ≤70 Per-Protocol Population

| | Full Population | | | ≤70 Population | | |
|---|---|---|---|---|---|---|
| Time | Median Placebo | Median Glyburide | p-value | Median Placebo | Median Glyburide | p-value |
| Day 90 | 25 | 55 | 0.16 | 25 | 60 | 0.06 |
| 6 Months | 32.5 | 50 | 0.23 | 32.5 | 60 | 0.12 |
| 12 Months | 30 | 50 | 0.12 | 30 | 75 | 0.03 |

Improvements on the EQ-5D

The EuroQol-5D (EQ-5D) is a generic instrument used to assess quality of life in a variety of conditions, including stroke. It is the most commonly used instrument in gathering cost-utility information in calculating quality of life adjusted years (QALY) in support of pricing and reimbursement discussions. It is one of the most widely used health-related quality of life instruments used in clinical studies. The minimal clinically important difference in stroke has been reported to be 0.08-0.12 units (Kim et al. 2015). In both the full per-protocol population and the ≤70 per-protocol population, the median difference between drug and placebo was greater than 0.12 at all time points. At 6 and 12 months, the difference was statistically significant in the ≤70 population.

TABLE 12

Comparison of Possible Effects on the EQ-5D in the Full vs. the ≤70 Per-Protocol Populations

| | Full Population | | ≤70 Population | |
|---|---|---|---|---|
| Time | Median Difference | p-value | Median Difference | p-value |
| 90 Days | 0.30 | 0.15 | 0.29 | 0.069 |
| 6 Months | 0.34 | 0.09 | 0.29 | 0.049 |
| 12 Months | 0.14 | 0.19 | 0.30 | 0.040 |

Treatment Timing

Unlike thrombolytic therapy for ischemic stroke, which relies on removing the clot and reperfusing tissue before it dies, anti-edema therapy should have a wider time-window because evolution of edema is part of a secondary response to the original insult. Brain herniation, the ultimate effect of this process, in fact, peaks 2-3 days following the injury. Based on the mechanism of action, which is based on affecting edema, rather than tissue sparing through reperfusion, there is no reason to anticipate a priori that time criticality would be evident in the first hours after the index stroke. Surprisingly, however, we did observe such an effect.

Using ordinal logistic regression, the mRS distribution in the entire per-protocol population was compared to the population who received drug in 9 hours or less (from the index stroke or the last time the subject was seen normal), and it was observed that an enhanced treatment effect in the form of an enhanced odds ratio (an odds ratio of 1 indicates no effect) was realized. The effect on mortality (survival) was similarly enhanced in an analysis using logistic regression. Accordingly, drug treatment in 9 hours or less, surprisingly, appears to be superior, despite the fact that there would be no expectation of time criticality at this point in the natural history of the condition.

TABLE 13

| | | Dosing ≤ 9 hours | |
|---|---|---|---|
| Population | N (P/D) | Mortality OR | mRS 0-6 OR |
| PP | 77 (36/41) | 2.75 | 1.91 |
| PP ≤ 9 hr | 33 (14/19) | 2.96 | 2.31 |

Specificity for Large Hemispheric Infarction

Figure 8:
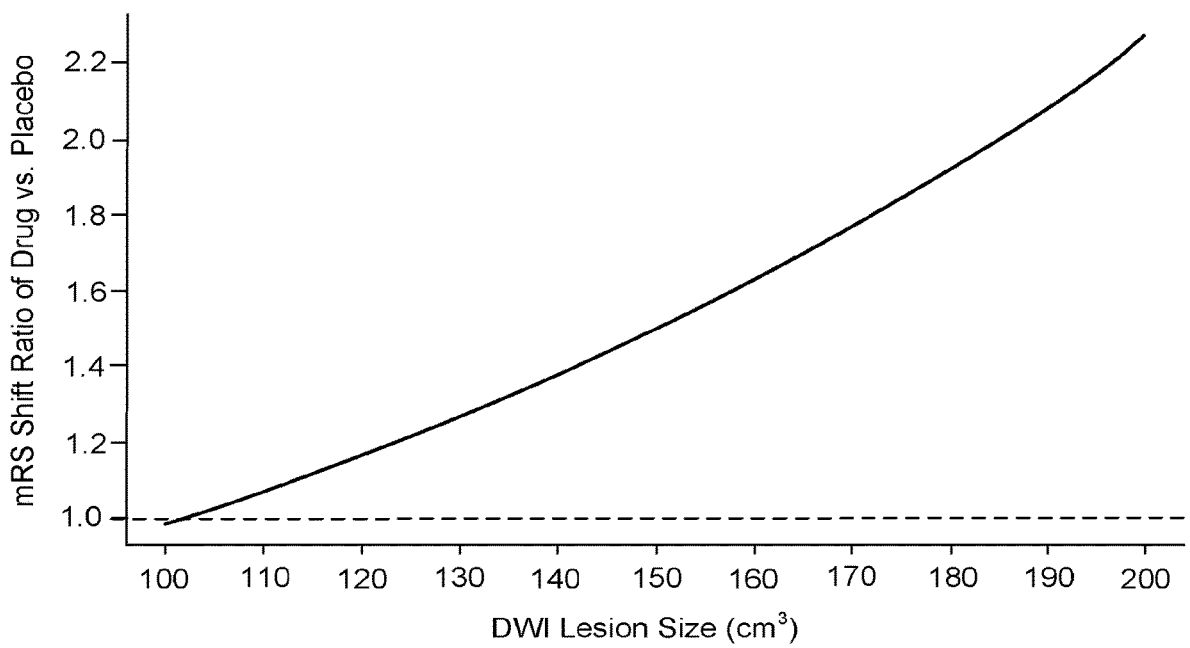
FIG. 8 shows analysis of mRS outcome as a function of lesion size in large hemispheric infarction.

While edema plays a part in a number of different conditions and is implicated in ischemic stroke generally, the clinical effects of treating edema in ischemic stroke may minimize to zero at some volume of infarction. Using the data from this study, the threshold lesion size below which outcomes are unaffected by drug treatment could be determined. More specifically, in this analysis, mRS "shift" was assessed as a function of increasing lesion size. The modified intent-to-treat population was utilized in order to include the broadest distribution of lesion sizes. Each 10 cc increase in baseline DWI lesion size (centrally adjudicated) was associated with an OR of 0.88 (p=0.026) in the placebo group, supporting prior observations that lesion size is a negative prognostic variable in terms of outcome. An interaction between treatment and lesion size yielded an OR of 1.09 (p=0.244) indicating that the treatment effect was greater with a larger lesion size, e.g., a 1.09-fold increase in the mRS "shift" per 10 cc increase in DWI size. By extrapolation, the "zero effect" lesion size of about 100 cc, the drug may not be expected to work as significantly in patients with smaller lesions, which is consistent with the fact that those patients are not likely to develop clinically meaningful edema in the first place. A larger lesion with greater edema may provide more dramatic results. This concept represented visually in FIG. 8, where a "zero effect" is indicated by an mRS shift OR of 1. In this instance, there was no shift below about 100 cc. More specifically, in patients with a baseline lesion ≤100 cc, the OR was calculated to be 1.00 (p=0.99), e.g., there was minimal to no effect of drug in lesions under 100 cc, supporting the findings of the interaction analysis.

Example 2—Randomized Double Blind Placebo Controlled Study in Traumatic Brain Injury A double-blind, placebo-controlled study to assess the effects of glyburide, as a representative SUR1-TRPM4 channel inhibitor, on edema in TBI was conducted at 3 clinical sites involving 29 subjects with moderate or severe TBI (Glasgow Coma Scale score 4-12) or with mild TBI (GCS 13-14) having hemorrhage on CT scan. The administration of the test drug was as follows: a bolus of 0.13 mg of the SUR1-TRPM4 channel inhibitor was administered over approximately 2 minutes followed by a continuous infusion of 0.16 mg/hr for 6 hours, and then a continuous infusion of 0.11 mg/hr for 66 hours, for a total dosing period of 72 hours. The total daily dose of Study Drug on Day 1, Day 2 and Day 3 was 3.12 mg, 2.67 mg, and 2.67 mg, respectively. All subjects were assessed by MRI scans at baseline and 72 hours.

The 14 subjects (7 drug and 7 placebo) identified as having evidence of lesional blood (i.e., blood associated with a contusion) at baseline and having MRI scans at both baseline and 72 hours were assessed for edema using MIM software version 5.6. Blinded readers ascertained x, y, z measurements of the total apparent contusion using T2 images, unless missing, in which case, DTI images were used. Only contusions that could be reliably measured (measuring at least about 1 cc) were measured. Readers also ascertained the volume measurements of hemorrhages in a similar manner using SWI images. Linear measurements were captured in centimeters (cm) and all volumes in cubic centimeters (cc). Volumes were calculated using the ABC/2 standard. The volume of apparent edema was calculated as the difference between the overall apparent contusion volume and the volume of the hemorrhage. For analysis, if there were multiple lesions, the volumes of all lesions meeting the threshold were combined.

The drug group at baseline had a larger mean volume of edema (8.72 ml versus 2.12 ml for placebo, a 4-fold difference) and worse clinical characteristics, as measured by the mean motor and eye domains of the Glasgow Coma Scale (GCS; 6.14 versus 7.67 in the placebo) and the rate of intubation (5 of 7 versus 3 of 7 in placebo). Despite this, the drug group showed less evolution of edema from baseline to 72 hours (2.14-fold growth versus 10.28-fold growth in placebo) and no difference in the mean Glasgow Coma Scale Extended score at 180 days (GOSE; 6 versus 6.17 for placebo). It can be concluded from these data that, despite a more severe clinical profile and 4-fold more edema at baseline than placebo, the drug substantially reduced the expansion or growth of edema and provided the same clinical outcomes as the placebo group. No drug-related effects were detected in non-lesioned subjects or in areas of the brain without a lesion, indicating the drug effect is surprisingly, not edema-specific, but specific to edema associated with a lesion.

It can be expected, therefore, that in a study consisting exclusively of subjects identified at baseline as having a radiologically-defined (e.g., CT or MRI) lesion that can be reliably measured (approximately 0.5 cc or more) and balanced in terms of baseline clinical characteristics, such as the GCS or its individual components (motor, eye, verbal), that the drug group would result in improved clinical outcomes on scales such as the GOSE with a minimum effect size of at least 4% or an odds ratio of at least 1.2, favoring drug over placebo.

Example 3—Control of Blood Glucose

Subjects treated with intravenous SUR1-TRPM4 inhibitor in accordance with the protocols described herein can be monitored and glucose controlled. Monitoring and treatment can be carried out, in one example, as follows:

Hourly (±30 min) the first 24 hours;
Every 2 hrs (±30 min) for hours 25 to 48; and
Every 4 hrs (±60 min) thereafter.

When blood glucose falls to less than about 70 mg/dL, monitoring frequency is in creased to every 15 min (±10 min) until blood glucose is 80 or more for 3 consecutive readings without exogenous glucose supplementation.

If drug is interrupted and resumed, blood glucose is measured hourly for about 3 hrs (±30 min). If no glucose is required, monitoring resumes to the previous frequency (e.g., at about 1, 2, or 4 hrs).

Blood glucose can further be controlled in subjects treated with an intravenous SUR1-TRPM4 inhibitor as follows:

If the blood glucose at baseline is less than 100 mg/dL, an initial maintenance fluid of about 5 wt % dextrose in normal saline (DSNS) at a rate of 70 to 100 cc/hr can be administered.

If blood glucose falls below about 100 mg/dL, DSNS is started at a rate of 70 to 100 cc/hr. Titration of the IV fluid rate up or down can be used to maintain blood glucose above about 80 mg/dL.

If blood glucose is less than 80 mg/dL, D5NS can be started, or if D5NS is already being administered, then the subject can be switched to about a 10 wt % dextrose in normal saline (D10NS).

If there is a rapid or continuous downward trend in blood glucose, D5NS is started, or if D5NS is already being administered, then the subject can be switched to D10NS.

In the event of blood glucose greater than about 140 mg/dL, D5NS or D10NS is not administered.

Any confirmed blood glucose of less than about 70 mg/dL can be treated with about a 50 mL ampule of dextrose 50 wt % in water (D50W). If D50W is not available, another concentration of dextrose fluid can be used at a sufficient volume to achieve an equivalent amount of dextrose.

Any of the above protocols or similar variants thereof can be described in various documentation associated with a pharmaceutical product. This documentation can include, without limitation, protocols, statistical analysis plans, investigator brochures, clinical guidelines, medication guides, risk evaluation and mediation programs, prescribing information and other documentation that may be associated with a pharmaceutical product. It is specifically contemplated that such documentation may be physically packaged with a SUR1-TRPM4 channel inhibitor pharmaceutical product as a kit, as may be beneficial or as set forth by regulatory authorities.

While the disclosure has been described with reference to certain examples, those skilled in the art will appreciate that various modifications, changes, omissions, and substitutions can be made without departing from the spirit of the disclosure. It is intended, therefore, that the disclosure, be limited only by the scope of the following claims.

The invention claimed is:

1. A method of reducing late neurological deterioration or death in a subject following a large hemispheric infarction, wherein the subject has a brain lesion volume of greater than 100 cc, comprising administering a glyburide to the subject, wherein the administering includes a first continuous infusion and a second continuous infusion of glyburide lasting cumulatively for at least 72 hours after starting the first continuous infusion, wherein the first continuous infusion is started within 9 hours following the subject experiencing the large hemispheric infarction.

2. The method of claim 1, comprising initiating administration of the glyburide within 1 hour following the subject experiencing the large hemispheric infarction.

3. The method of claim 1, comprising initiating administration of the glyburide within 4½ hours following the subject experiencing the large hemispheric infarction.

4. The method of claim 1, comprising initiating administration of the glyburide prior to about 8 hours following the subject experiencing the large hemispheric infarction.

5. The method of claim 1, wherein administering the continuous infusions of glyburide occur for at least 96 hours.

6. The method of claim 1, wherein administering the continuous infusions of glyburide occur for at least 120 hours.

7. The method of claim 1, wherein the first continuous infusion is started after a bolus dose administration.

8. The method of claim 1, wherein the first continuous infusion has a higher dosage concentration than the second continuous infusion.

9. The method of claim 1, wherein administering of glyburide is coupled with a decompressive craniectomy.

10. A method of reducing cerebral midline shift in a subject following a large hemispheric infarction, wherein the subject has a brain lesion volume of greater than 100 cc, comprising:
administering to the subject glyburide following the subject experiencing the large hemispheric infarction, wherein the administering includes a first continuous infusion and a second continuous infusion of glyburide lasting cumulatively for at least 72 hours after starting the first continuous infusion, wherein the first continuous infusion is started within 9 hours following the subject experiencing the large hemispheric infarction, wherein the method reduces the cerebral midline shift as determined over a population based on the degree of cerebral midline shift in patients treated with the continuous infusions compared to a similar population that was not treated with the continuous infusions.

11. The method of claim 10, wherein administering glyburide includes one or more continuous infusion lasting cumulative for at least 72 hours.

12. The method of claim 10, wherein administering glyburide includes one or more continuous infusion lasting cumulatively for at least 96 hours.

13. The method of claim 10, wherein the first continuous infusion is started after a bolus dose administration.

14. The method of claim 10, wherein the first continuous infusion has a higher dosage concentration than the second.

15. The method of claim 1, further comprising measuring blood glucose levels before or during the administering step.

16. The method of claim 15, further comprising detecting a blood glucose level in the subject of at or below about 120 mg/dL and administering a dextrose solution to the subject.

17. The method of claim 15, further comprising detecting a blood glucose level in the subject of at or below about 100 mg/dL and administering a dextrose solution to the subject.

18. The method of claim 15, further comprising detecting a blood glucose level in the subject of greater than about 80 mg/dL to 100 mg/dL and administering a 3 wt % to 8 wt % solution of dextrose to the subject at from about 50 cc/hr to about 120 cc/hr.

19. The method of claim 15, further comprising detecting a blood glucose level in the subject of about 55 mg/dL to 80 mg/dL and administering an 8 wt % to 12 wt % solution of dextrose to the subject at from 50 cc/hr to 120 cc/hr.

20. The method of claim 15, further comprising detecting a blood glucose level in the subject of less 55 mg/dL, and administering an 8 wt % to 12 wt % solution of dextrose to the subject at from 50 cc/hr to 120 cc/hr.

* * * * *